(12) United States Patent
Chen et al.

(10) Patent No.: US 10,060,903 B2
(45) Date of Patent: Aug. 28, 2018

(54) EXPORTING MEASUREMENTS OF NANOPORE ARRAYS

(71) Applicant: Genia Technologies, Inc., Mountain View, CA (US)

(72) Inventors: Roger J. A. Chen, Saratoga, CA (US); Hui Tian, Cupertino, CA (US); Santiago Fernandez-Gomez, Sunnyvale, CA (US)

(73) Assignee: Genia Technologies, Inc., Santa Clara, CA (US)

(*) Notice: Subject to any disclaimer, the term of this patent is extended or adjusted under 35 U.S.C. 154(b) by 209 days.

(21) Appl. No.: 14/534,042

(22) Filed: Nov. 5, 2014

(65) Prior Publication Data

US 2016/0123923 A1    May 5, 2016

(51) Int. Cl.
| | |
|---|---|
| *G01N 27/447* | (2006.01) |
| *G01N 27/22* | (2006.01) |
| *G01N 33/487* | (2006.01) |
| *C12Q 1/6869* | (2018.01) |
| *B82Y 15/00* | (2011.01) |

(52) U.S. Cl.
CPC ..... *G01N 33/48721* (2013.01); *C12Q 1/6869* (2013.01); *B82Y 15/00* (2013.01)

(58) Field of Classification Search
CPC ........ G01N 33/48721; G01N 33/48728; B03C 5/00–5/028

USPC ............... 204/450–470, 547–549, 600–621, 204/644–648; 205/792
See application file for complete search history.

(56) References Cited

U.S. PATENT DOCUMENTS

| | | |
|---|---|---|
| 2003/0099951 A1 | 5/2003 | Akeson et al. |
| 2007/0048745 A1 | 3/2007 | Joyce et al. |
| 2010/0292101 A1 | 11/2010 | So |
| 2012/0020537 A1 | 1/2012 | Garcia et al. |
| 2012/0091005 A1* | 4/2012 | Burrows ............ B82Y 15/00 204/605 |
| 2013/0240359 A1 | 9/2013 | Turner et al. |
| 2014/0134616 A1 | 5/2014 | Davis et al. |

* cited by examiner

*Primary Examiner* — Bach T Dinh
(74) *Attorney, Agent, or Firm* — Van Pelt, Yi & James LLP

(57) ABSTRACT

A method of exporting measurements of a nanopore sensor on a nanopore based sequencing chip is disclosed. An electrical characteristic associated with the nanopore sensor is measured. The electrical characteristic associated with the nanopore sensor is processed. A summary for the electrical characteristic and one or more previous electrical characteristics is determined. The summary for the electrical characteristic and the one or more previous electrical characteristics are exported. Determining the summary includes determining that the electrical characteristic and at least a portion of the one or more previous electrical characteristics correspond to a base call event at the nanopore sensor. The summary represents the electrical characteristic and the at least a portion of the one or more previous electrical characteristics.

9 Claims, 8 Drawing Sheets

EXPORTING MEASUREMENTS OF NANOPORE ARRAYS

BACKGROUND OF THE INVENTION

Advances in micro-miniaturization within the semiconductor industry in recent years have enabled biotechnologists to begin packing traditionally bulky sensing tools into smaller and smaller form factors, onto so-called biochips. It would be desirable to develop techniques for biochips that make them more robust, efficient, and cost-effective.

BRIEF DESCRIPTION OF THE DRAWINGS

Various embodiments of the invention are disclosed in the following detailed description and the accompanying drawings.

DETAILED DESCRIPTION

The invention can be implemented in numerous ways, including as a process; an apparatus; a system; a composition of matter; a computer program product embodied on a computer readable storage medium; and/or a processor, such as a processor configured to execute instructions stored on and/or provided by a memory coupled to the processor. In this specification, these implementations, or any other form that the invention may take, may be referred to as techniques. In general, the order of the steps of disclosed processes may be altered within the scope of the invention. Unless stated otherwise, a component such as a processor or a memory described as being configured to perform a task may be implemented as a general component that is temporarily configured to perform the task at a given time or a specific component that is manufactured to perform the task. As used herein, the term 'processor' refers to one or more devices, circuits, and/or processing cores configured to process data, such as computer program instructions.

A detailed description of one or more embodiments of the invention is provided below along with accompanying figures that illustrate the principles of the invention. The invention is described in connection with such embodiments, but the invention is not limited to any embodiment. The scope of the invention is limited only by the claims and the invention encompasses numerous alternatives, modifications and equivalents. Numerous specific details are set forth in the following description in order to provide a thorough understanding of the invention. These details are provided for the purpose of example and the invention may be practiced according to the claims without some or all of these specific details. For the purpose of clarity, technical material that is known in the technical fields related to the invention has not been described in detail so that the invention is not unnecessarily obscured.

Nanopore membrane devices having pore sizes on the order of one nanometer in internal diameter have shown promise in rapid nucleotide sequencing. When a voltage potential is applied across a nanopore immersed in a conducting fluid, a small ion current attributed to the conduction of ions across the nanopore can be observed. The size of the current is sensitive to the pore size.

A nanopore based sequencing chip may be used for DNA sequencing. A nanopore based sequencing chip incorporates a large number of sensor cells configured as an array. For example, an array of one million cells may include 1000 rows by 1000 columns of cells.

Figure 1:
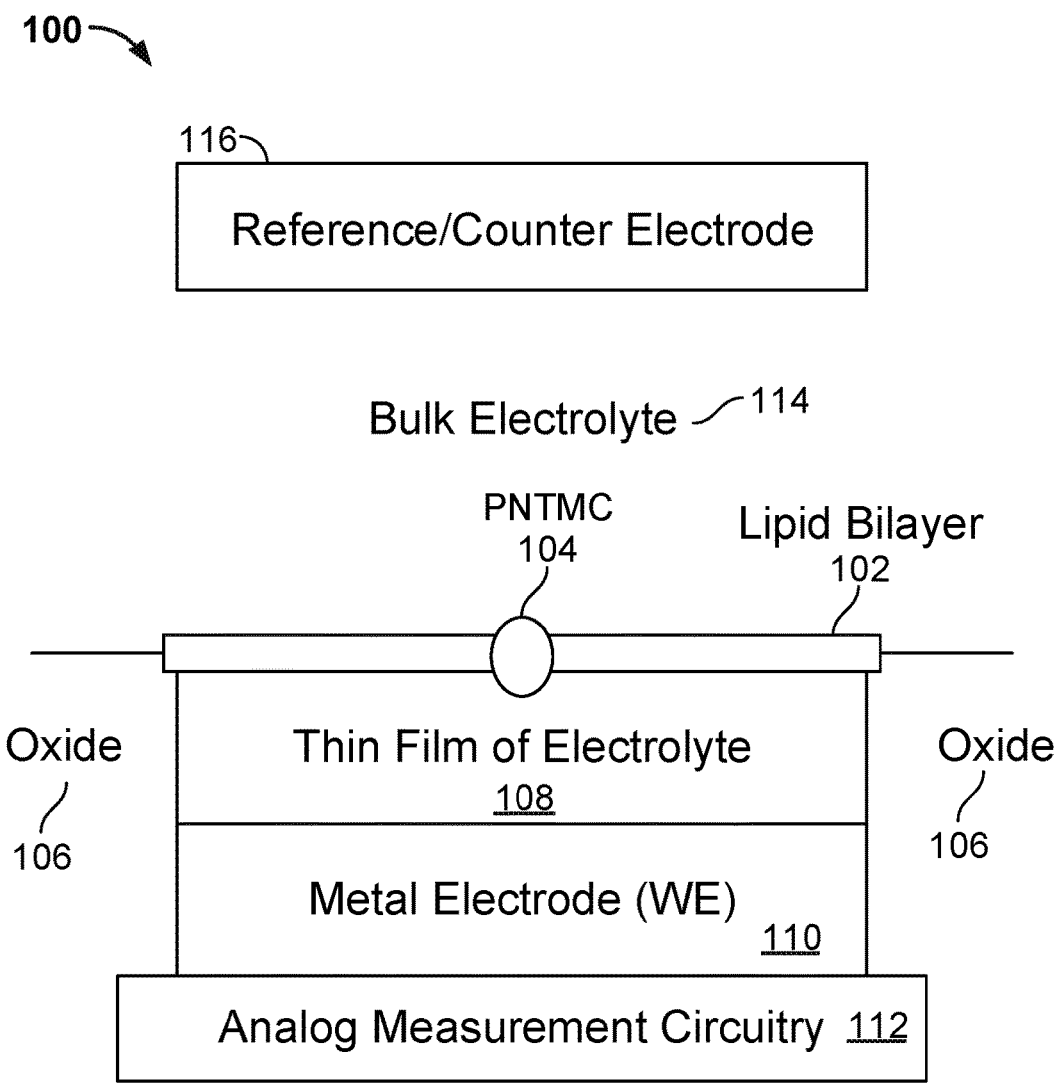
FIG. 1 illustrates an embodiment of a cell 100 in a nanopore based sequencing chip.

FIG. 1 illustrates an embodiment of a cell 100 in a nanopore based sequencing chip. A lipid bilayer 102 is formed over the surface of the cell. The bulk electrolyte 114 containing soluble protein nanopore transmembrane molecular complexes (PNTMC) and the analyte of interest is placed directly onto the surface of the cell. A single PNTMC 104 is inserted into lipid bilayer 102 by electroporation. The individual lipid bilayers in the array are not connected to each other either chemically or electrically. Thus, each cell in the array is an independent sequencing machine, producing data unique to the single polymer molecule associated with the PNTMC. PNTMC 104 operates on the analytes and modulates the ionic current through the otherwise impermeable bilayer.

With continued reference to FIG. 1, analog measurement circuitry 112 is connected to a metal electrode 110 covered by a thin film of electrolyte 108. The thin film of electrolyte 108 is isolated from the bulk electrolyte 114 by the ion-impermeable lipid bilayer 102. PNTMC 104 crosses lipid bilayer 102 and provides the only path for ionic current to flow from the bulk liquid to metal electrode 110. Metal electrode 110 is also referred to as the working electrode (WE). The cell also includes a counter/reference electrode (CE/RE) 116, which is an electrochemical potential sensor.

Figure 2:
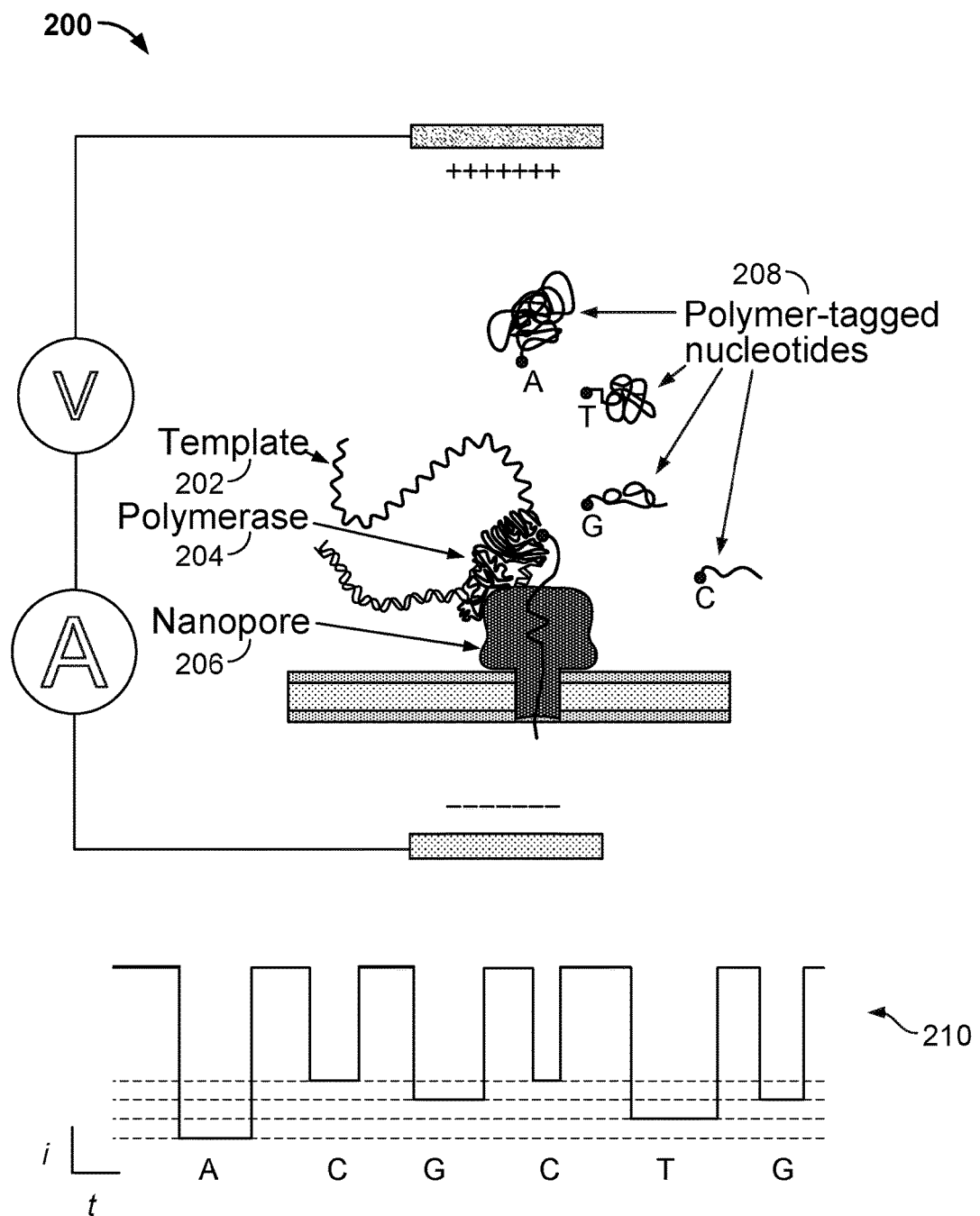
FIG. 2 illustrates an embodiment of a cell 200 performing nucleotide sequencing with the Nano-SBS technique.

In some embodiments, a nanopore array enables parallel sequencing using the single molecule nanopore-based sequencing by synthesis (Nano-SBS) technique. FIG. 2 illustrates an embodiment of a cell 200 performing nucleotide sequencing with the Nano-SBS technique. In the Nano-SBS technique, a template 202 to be sequenced and a primer are introduced to cell 200. To this template-primer complex, four differently tagged nucleotides 208 are added to the bulk aqueous phase. As the correctly tagged nucleotide is complexed with the polymerase 204, the tail of the tag is positioned in the barrel of nanopore 206. After polymerase catalyzed incorporation of the correct nucleotide, the tag-attached polyphosphate held in the barrel of nanopore 206 generates a unique ionic current blockade signal 210, thereby identifying the added base electronically due to the tags' distinct chemical structures.

Figure 3:
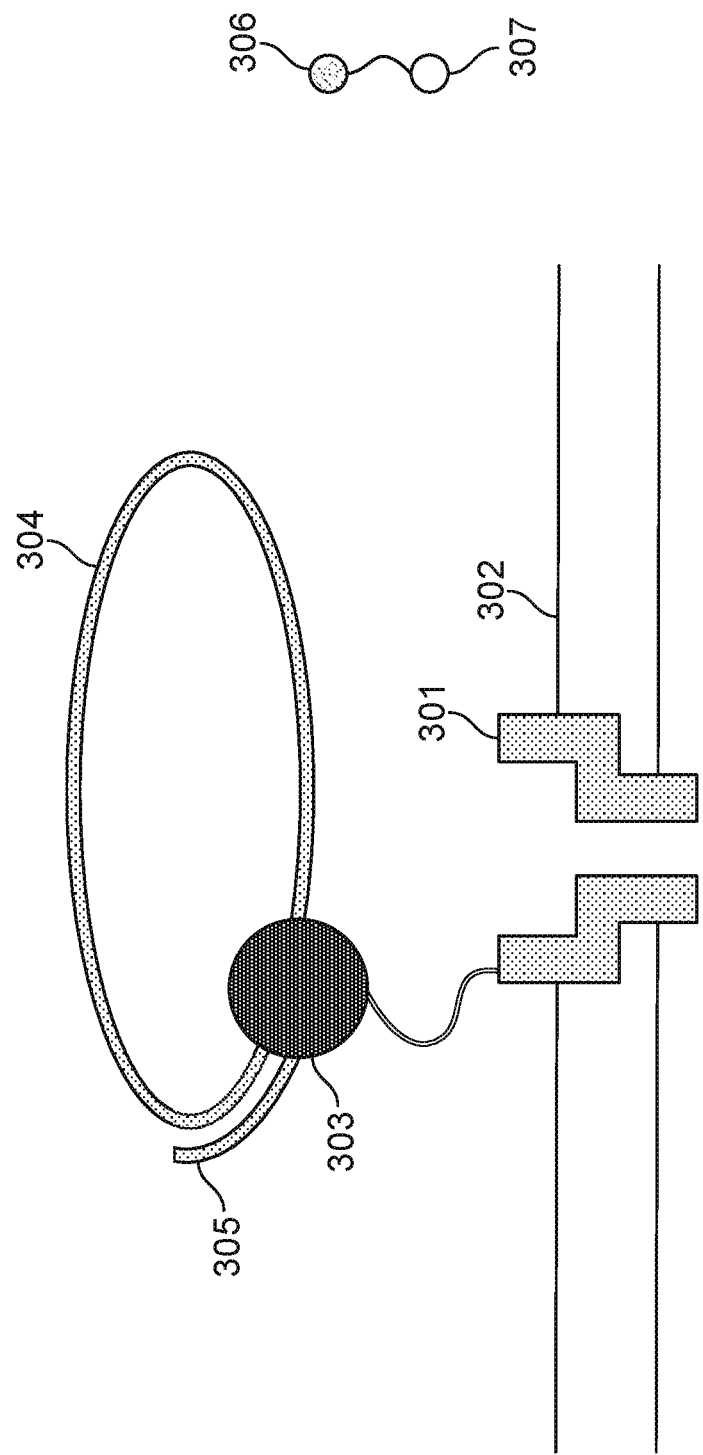
FIG. 3 illustrates an embodiment of a cell performing nucleotide sequencing with pre-loaded tags.

FIG. 3 illustrates an embodiment of a cell about to perform nucleotide sequencing with pre-loaded tags. A nanopore 301 is formed in a membrane 302. An enzyme 303 (e.g., a polymerase, such as a DNA polymerase) is associated with the nanopore. In some cases, polymerase 303 is covalently attached to nanopore 301. Polymerase 303 is associated with a single stranded nucleic acid molecule 304 to be sequenced. In some embodiments, single or double stranded nucleic acid molecule 304 is circular. In some cases, nucleic acid molecule 304 is linear. In some embodiments, a nucleic acid primer 305 is hybridized to a portion of nucleic acid molecule 304. Polymerase 303 catalyzes the incorporation of nucleotides 306 onto primer 305 using single stranded nucleic acid molecule 304 as a template. Nucleotides 306 comprise tag species ("tags") 307.

Figure 4:
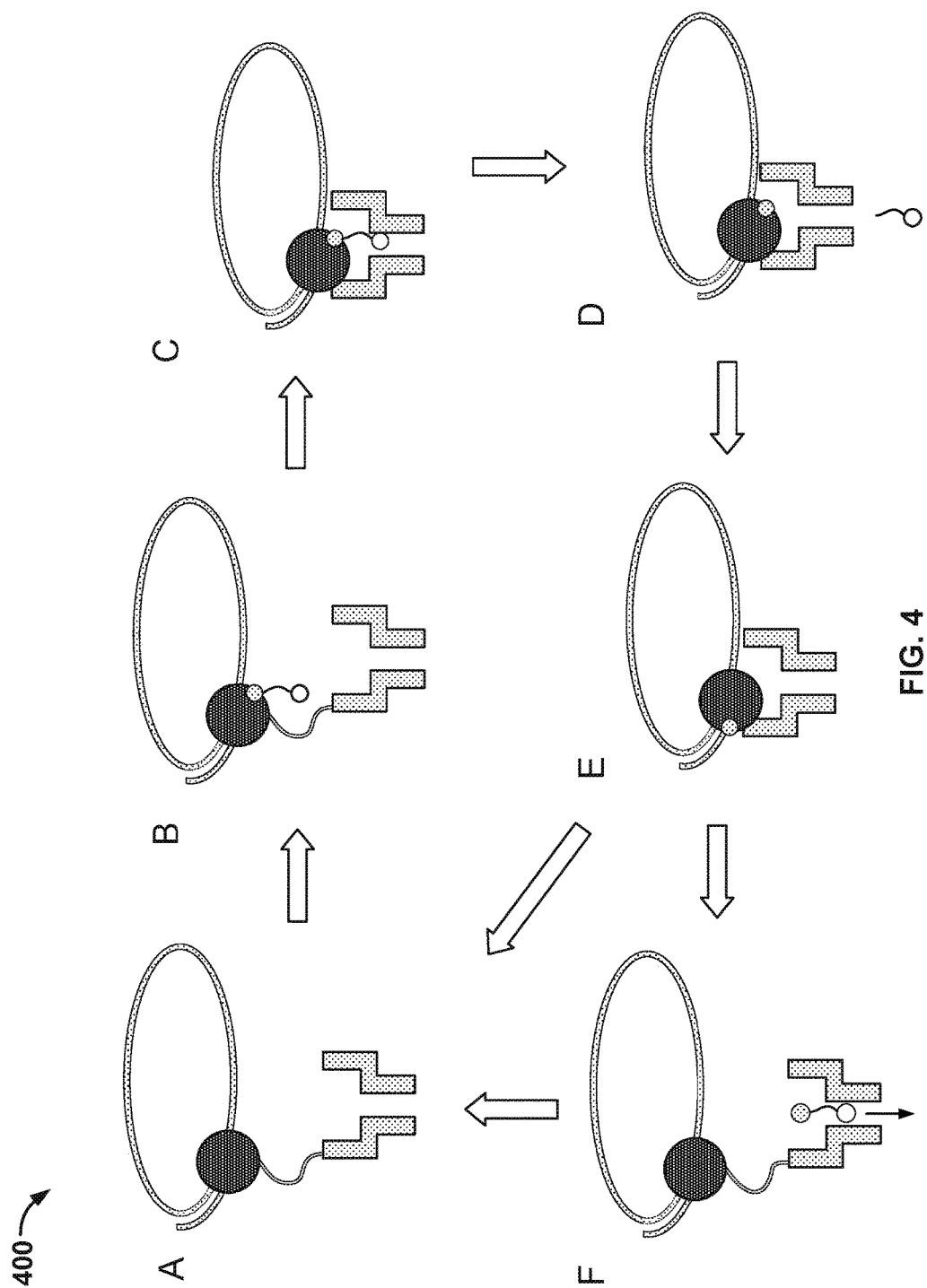
FIG. 4 illustrates an embodiment of a process 400 for nucleic acid sequencing with pre-loaded tags.

FIG. 4 illustrates an embodiment of a process 400 for nucleic acid sequencing with pre-loaded tags. Stage A illustrates the components as described in FIG. 3. Stage C shows the tag loaded into the nanopore. A "loaded" tag may be one that is positioned in and/or remains in or near the nanopore for an appreciable amount of time, e.g., 0.1 millisecond (ms) to 1000 ms. In some cases, a tag that is pre-loaded is loaded in the nanopore prior to being released from the nucleotide. In some instances, a tag is pre-loaded if the probability of the tag passing through (and/or being detected by) the nanopore after being released upon a nucleotide incorporation event is suitably high, e.g., 90% to 99%.

At stage A, a tagged nucleotide (one of four different types: A, T, G, or C) is not associated with the polymerase. At stage B, a tagged nucleotide is associated with the polymerase. At stage C, the polymerase is docked to the nanopore. The tag is pulled into the nanopore during docking by an electrical force, such as a force generated in the presence of an electric field generated by a voltage applied across the membrane and/or the nanopore.

Some of the associated tagged nucleotides are base paired with the single stranded nucleic acid molecule (e.g., A with T and G with C). However, some of the associated tagged nucleotides are not base paired with the single stranded nucleic acid molecule. These non-paired nucleotides typically are rejected by the polymerase within a time scale that is shorter than the time scale for which correctly paired nucleotides remain associated with the polymerase. Since the non-paired nucleotides are only transiently associated with the polymerase, process 400 as shown in FIG. 4 typically does not proceed beyond stage D. For example, a non-paired nucleotide is rejected by the polymerase at stage B or shortly after the process enters stage C.

Before the polymerase is docked to the nanopore, the current passing through the nanopore is ~30 picoamps (pA). At stage C, the current flowing through the nanopore is about 6 pA, 8 pA, 10 pA, or 12 pA, each amperage corresponding to one of the four types of tagged nucleotides. The polymerase undergoes an isomerization and a transphosphorylation reaction to incorporate the nucleotide into the growing nucleic acid molecule and release the tag molecule. At stage D, the released tag passes through the nanopore. The tag is detected by the nanopore. In particular, as the tag is held in the nanopore, a unique ionic current blockade signal (e.g., see signal 210 in FIG. 2) is generated due to the tag's distinct chemical structures, thereby identifying the added base electronically. Repeating the cycle (i.e., stage A through E or stage A through F) allows for the sequencing of the nucleic acid molecule.

In some cases, tagged nucleotides that are not incorporated into the growing nucleic acid molecule will also pass through the nanopore, as seen in stage F of FIG. 4. The unincorporated nucleotide can be detected by the nanopore in some instances, but the method provides a means for distinguishing between an incorporated nucleotide and an unincorporated nucleotide based at least in part on the time for which the nucleotide is detected in the nanopore. Tags bound to unincorporated nucleotides pass through the nanopore quickly and are detected for a short period of time (e.g., less than 10 ms), while tags bound to incorporated nucleotides are loaded into the nanopore and detected for a long period of time (e.g., at least 10 ms).

Figure 5:
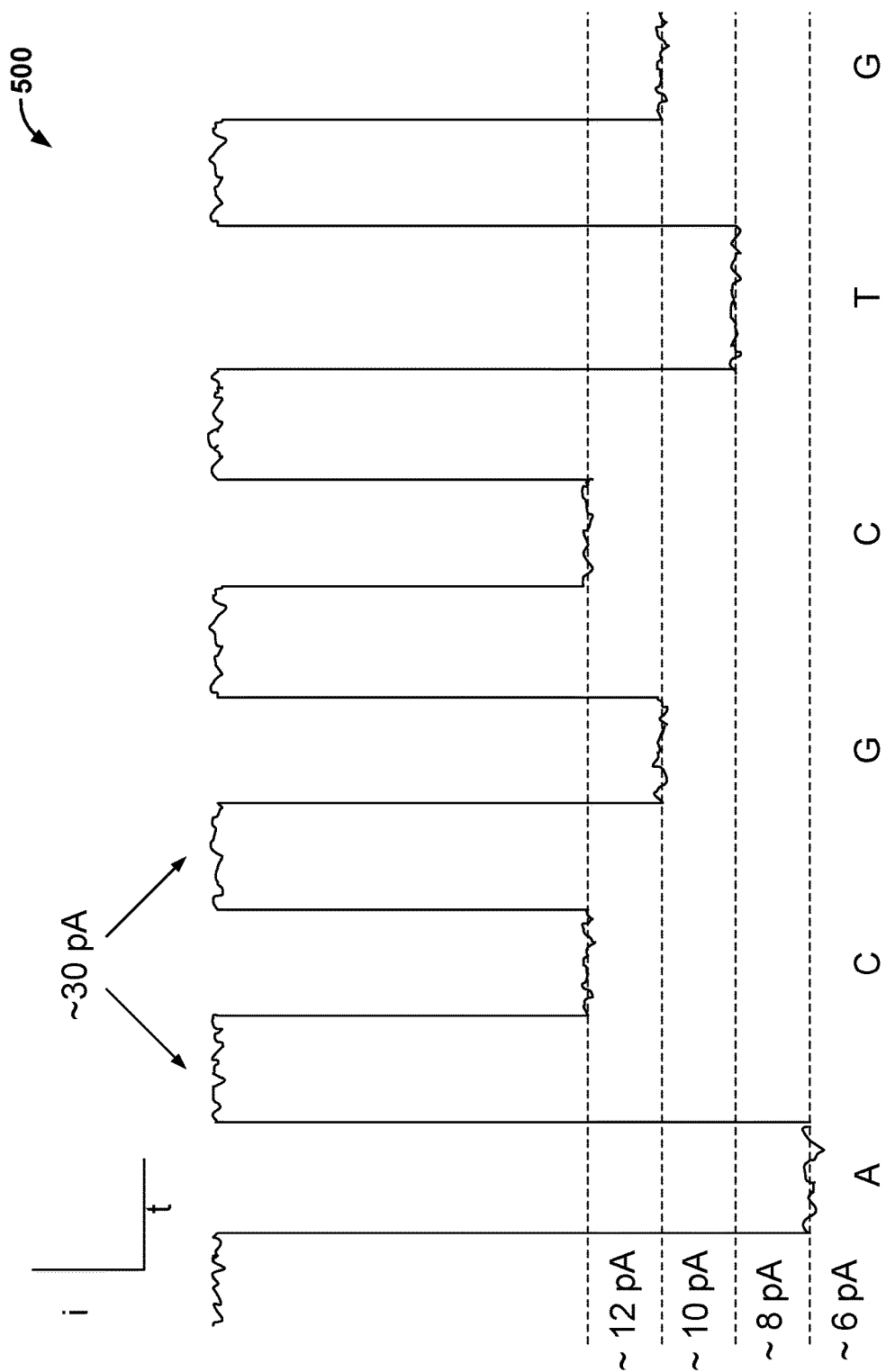
FIG. 5 illustrates an embodiment of an ionic current blockade signal 500 that is measured in a cell of a nanopore based sequencing chip.

FIG. 5 illustrates an embodiment of an ionic current blockade signal 500 that is measured in a cell of a nanopore based sequencing chip. For example, in the embodiments in which each cell performs nucleotide sequencing with the Nano-SBS technique as shown in FIG. 2, ionic current blockade signal 500 is the measured signal as different tag-attached polyphosphates are held in the barrel of nanopore 206.

As shown in FIG. 5, the y-axis is the measured ionic current blockade signal, and the x-axis is time. When the polymerase is not docked to the nanopore, the nanopore is referred to as being in an open channel state. When there is an open channel at the nanopore, the current passing through the nanopore is ~30 pA. When the polymerase is docked to the nanopore, the current flowing through the nanopore is about 6 pA, 8 pA, 10 pA, or 12 pA, each amperage corresponding to one of the four types of tagged nucleotides: A, T, G, or C. Although the four current levels (~6 pA, ~8 pA, ~10 pA, and ~12 pA) may vary from site to site, may drift in magnitude over time and may have varying amounts of noise associated with them, the four current levels are separate from each other and distinguishable from each other. Thus, after adjustments are made to offset the drift in magnitude over time and the noise associated with the measured current, four distinct current levels may be used as signature current levels for identifying the four different types of tagged nucleotides. For example, the events that can be detected from ionic current blockade signal 500 by matching the signal with the signature current levels include the detection of the tagged nucleotides A, C, G, C, T, and G, as shown in FIG. 5. Detecting A, C, G, C, T, or G is hereinafter referred to as base calling, and the event of detecting a tagged nucleotide (e.g., detecting A) is referred to as a base call event.

In some embodiments, the ionic current is read by analog measurement circuit 112 (see FIG. 1) in each cell, converted to digital information and transmitted out of the chip, and base calling may be performed outside of the chip by a computer. In some embodiments, a field programmable gate array (FPGA) or application-specific integrated circuit (ASIC) receives the transmitted data, processes the data, and forwards the data out of the chip to a computer, where base calling techniques may be performed. However, as the nanopore based sequencing chip is scaled to include more and more cells, the aggregate transmission data rate to and from the nanopore based sequencing chip may increase to an unattainable rate. For example, if a single cell generates 10,000 samples per second at 8 bits/sample, then a nanopore based sequencing chip with ten million cells would generate about 100 gigabytes of data per second. And if the nanopore based sequencing chip runs for about thirty minutes, then the total amount of data would accumulate to about 200 terabytes.

The aggregate transmission data rate of the nanopore based sequencing chip may be reduced by a number of ways. In some embodiments, digital compression techniques may be used to compress some of the data on the nanopore based sequencing chip, and then the compressed data may be transmitted out of the chip at a lower transmission rate, as will be described in greater detail below.

In some embodiments, data reduction is achieved by filtering groups of data in the time domain. Static and dynamic calibration helps achieve data compression and filtering on-chip. A number of memory and memory-less effects are addressed using calibration, in particular but not limited to: silicon process variation at array and cell level, electrode variation, lipid and biochemistry characteristics and variations from sample to sample, temperature and voltage variation effects, system memory effects in regards to sequences, optimal read-out windows, and aging effects throughout a complete sequencing cycle.

Calibration allows for dynamic establishment and identification of electrical levels, and alignment/tracking throughout a complete sample sequencing cycle so filtering/compression schemes remain fully effective and accurate. It also allows for determination of optimal reading parameters, and times, and identifying irregularities in the sample that cannot otherwise be understood by simply looking at filtered/compressed data.

The calibration strategies include static and dynamic techniques, cell-based and array-based, random sampling, the use of side-band signals in parallel to data capture, RAW data capture, and extrapolation based on open channel levels.

In some embodiments, some of the data may be processed (e.g., using base-calling techniques) on the nanopore based sequencing chip. The processed data may then be transmitted out of the chip, e.g., to a computer for further processing. Alternatively, the processed data may be used by the nanopore based sequencing chip for detecting events and generating control signals in response to the detected events. The generated control signals may be fed back into the individual cells or groups of cells as input control signals. Because some of the detections and decisions are made on-chip, less data is required to be transmitted out of the chip for further processing and less control data may be transmitted to the chip, and the response time for generating the control data may also be reduced.

Figure 6:
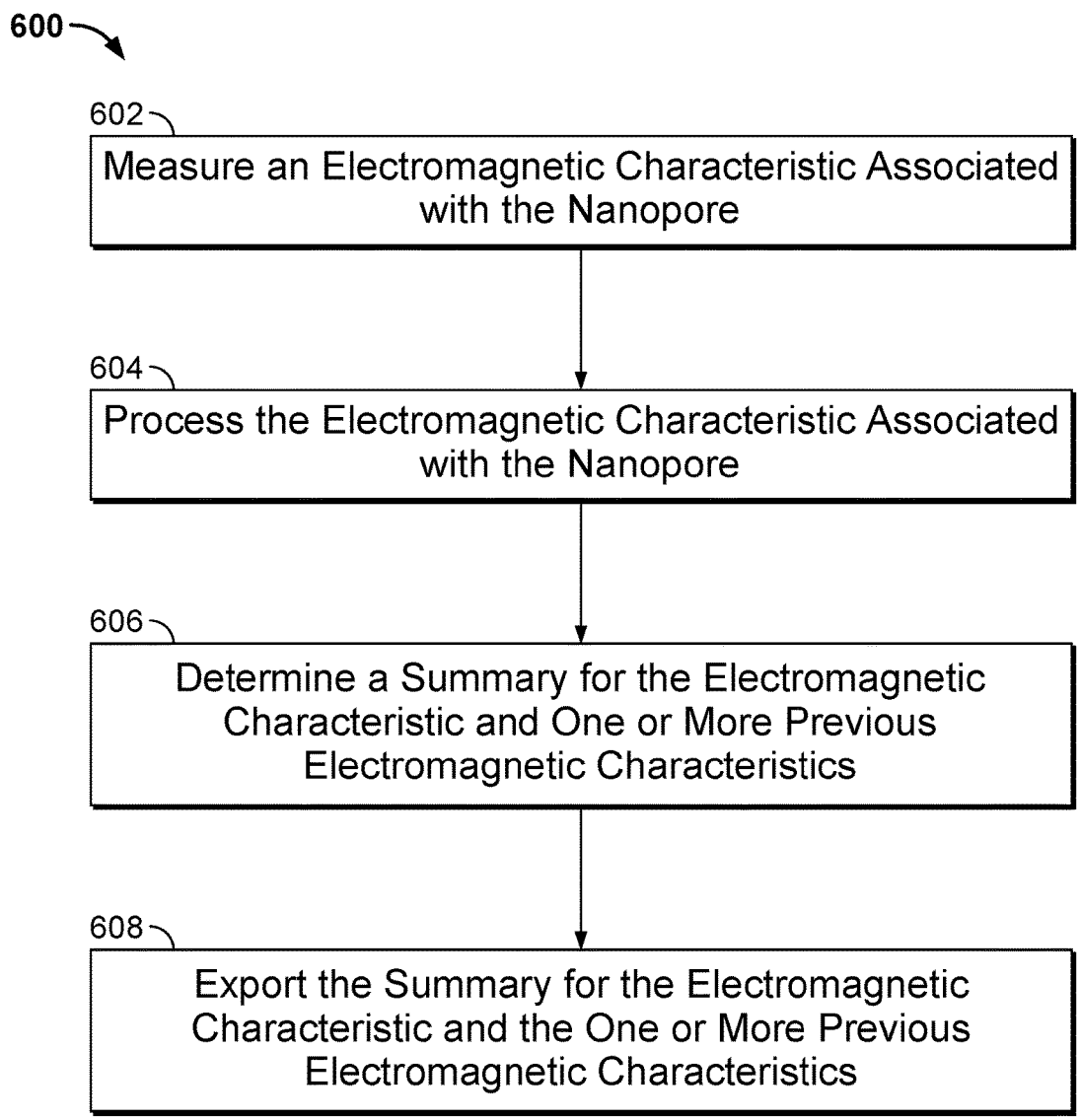
FIG. 6 illustrates a flow diagram of an embodiment of a process 600 for exporting measurements of a nanopore sensor on a nanopore based sequencing chip.

FIG. 6 illustrates a flow diagram of an embodiment of a process 600 for exporting measurements of a nanopore sensor on a nanopore based sequencing chip. At 602, an electrical characteristic associated with a nanopore sensor in a cell of a nanopore based sequencing chip is measured. In some embodiments, the electrical characteristic associated with the nanopore sensor that is measured includes a current. For example, referring back to FIG. 2, after polymerase catalyzed incorporation of the correct nucleotide, the tag-attached polyphosphate held in the barrel of nanopore 206 generates a unique ionic current blockade signal 210 that can be measured. In some embodiments, other types of electrical characteristics associated with the nanopore sensor may be measured, including the voltage, capacitance, or resistance associated with the nanopore sensor or portions of the nanopore sensor or cell.

At 604, the electrical characteristic associated with the nanopore sensor is processed. In some embodiments, processing of the nanospore sensor electrical characteristic includes reducing the noise associated with the measurements. For example, noise may be reduced by averaging the measurements. Noise may also be reduced by filtering techniques. In some embodiments, processing includes monitoring and offsetting the drift of the electrical characteristic in magnitude over time, such that distinct levels of the electrical characteristic may be used as signature levels for identifying the different types of tagged nucleotides. In some embodiments, the measurements of the electrical characteristic may be adjusted to offset the drift effect. In some embodiments, the signature levels for identifying the different types of tagged nucleotides may be adjusted dynamically to offset the drift of the electrical characteristic being measured. A signature level for identifying a particular type of tagged nucleotides may include a pair of upper and lower thresholds. For example, if the electrical characteristic falls within the upper and lower threshold levels, then it may be mapped to the particular signature level and its corresponding base call event (e.g., detecting A, C, G, or T).

In some embodiments, the correction of the drift effect may be performed on the nanopore based sequencing chip. In some embodiments, the correction of the drift effect may be performed outside of the nanopore based sequencing chip. For example, an external computer may receive and monitor the ionic current measurements, and determine the amount of correction of the drift effect over time. The external computer may send control signals to the nanopore based sequencing chip to correct the drift effect dynamically.

In some embodiments, the correction of the drift effect may be performed at the cell level. Each cell includes logic components to monitor and offset the drift effect as described above. In some embodiments, the correction of the drift effect may be performed independently within different regions of the nanopore based sequencing chip. This is because the amount of drift may vary within different regions of the chip. Each region may include logic components to monitor and offset the drift effect of the cells within that region collectively.

At 606, a summary for the electrical characteristic and one or more previous electrical characteristics is determined. At 608, a summary for the electrical characteristic and the one or more previous electrical characteristics is exported from the nanopore based sequencing chip. The exported summary may be used by a computer for further processing. As will be described in greater detail below, the summary extracts from the measurements of the electrical characteristics the information that enables the detection of base call events and excludes information that is not useful for base calling. The summary is a compression of the electrical characteristics and is more compact than the measurements of the electrical characteristics. As a result, exporting the summary, as opposed to exporting the measurements, reduces the aggregate transmission data rate of the nanopore based sequencing chip.

Figure 7:
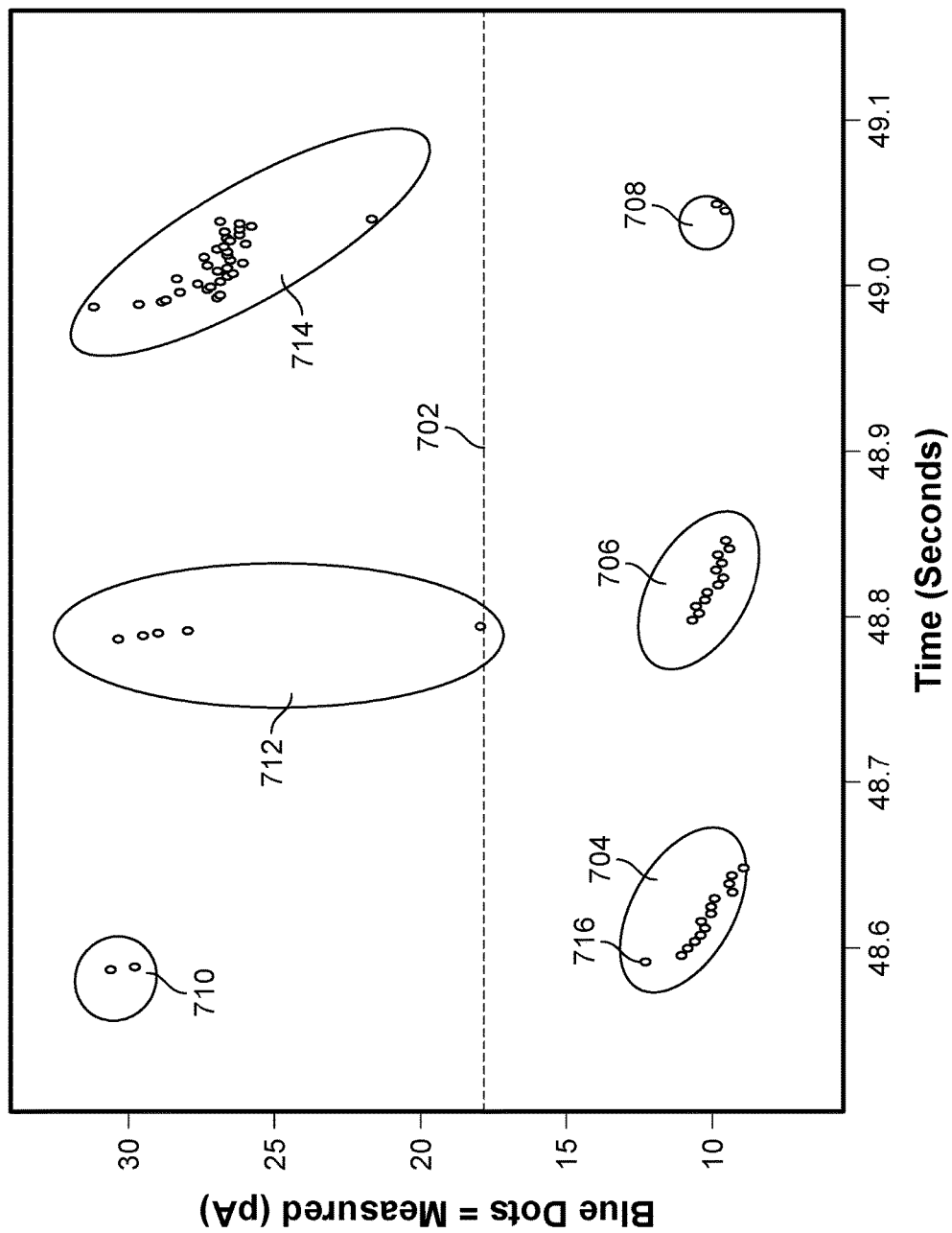
FIG. 7 illustrates an exemplary set of measurements of the ionic current blockade signal in a cell of the nanopore based sequencing chip.

FIG. 7 illustrates an exemplary set of measurements of the ionic current blockade signal in a cell of the nanopore based sequencing chip. The y-axis is the measured ionic current blockade signal, and the x-axis is time. Different ways to determine the summary for the measurement data will be discussed below using the set of measurements as shown in FIG. 7 as an illustrative example.

Figure 8:
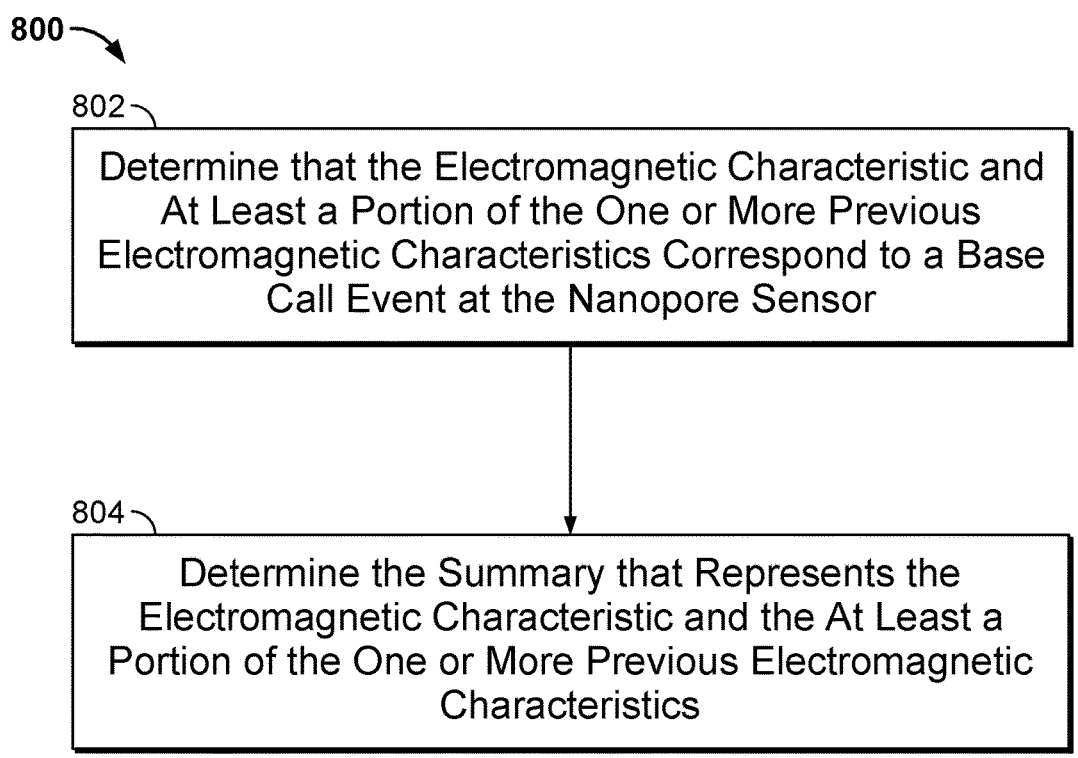
FIG. 8 illustrates a flow chart of an embodiment of a process 800 for determining a summary for the measurements of the ionic current blockade signal in a cell of the nanopore based sequencing chip.

FIG. 8 illustrates a flow chart of an embodiment of a process 800 for determining a summary for some of the measurements of the ionic current blockade signal in a cell of the nanopore based sequencing chip. In some embodiments, process 800 is a process that is performed at step 606 of FIG. 6.

At 802, it is determined that the electrical characteristic and at least a portion of the one or more previous electrical characteristics correspond to a base call event at the nanopore sensor. For example, as shown in FIG. 7, measurements 704 may be determined as corresponding to a base call event of detecting the tagged nucleotide of type G because the measurements may be mapped to the signature level of 10 pA. Similarly, measurements 706 and 708 may be determined as corresponding to two additional base call events of again detecting the tagged nucleotide of type G.

A number of criteria may be used to determine that a plurality of measurements corresponds to a single base call event. For example, if nucleotide sequencing is performed with the Nano-SBS technique, then it is known that two base call events are separated from each other by an open channel state, which has a significantly higher signature current level (~30 pA). Therefore, measurements that are above a threshold level 702 may be determined as corresponding to open channel states. While these measurements may not provide additional information useful for base calling, they may be used to separate segments of measurements. For example, measurements that are between measurements 710 and 712, i.e., measurements 704, may be determined as corresponding to a single base call event, and measurements that are between measurements 712 and 714, i.e., measurements 706, may be determined as corresponding to another base call event.

With continued reference to FIG. 8, at 804, the summary that represents the electrical characteristic and the at least a portion of the one or more previous electrical characteristics is determined. In some embodiments, the summary includes a magnitude parameter and a time parameter. For example, the magnitude parameter may be the average magnitude of the electrical characteristics, and the time parameter may be the duration of the measurements. For example, with reference to FIG. 7, the first parameter representing measurements 704 is 10 pA and the second parameter is 57 ms. Similarly, the parameters representing measurements 706 and 708 are (10 pA, 48 ms) and (10 pA, 8 ms), respectively. The original measurements before compression include 79 measurements of one byte each. After compression, the summary representing the measurements is reduced to 6 bytes of data. Therefore, the compression ratio is more than 10:1.

In some embodiments, the summary is determined by run-length encoding. For example, consecutive measurements that are mapped to a certain threshold may be represented by a single magnitude value and a count of the consecutive measurements.

In some embodiments, the summary is determined by encoding the time duration of measurements at a certain level. For example, consecutive measurements that are mapped to a certain threshold may be represented by a single magnitude value and a time duration of the consecutive measurements.

In some embodiments, the summary is determined by encoding the beginning of a base call event. For example, the first measurement (see measurement 716) after an open channel state may be used to represent the base call event.

In some embodiments, base calling is performed at step 606 of process 600. The summary includes the base call events. For example, the summary for the measurements shown in FIG. 7 is (G, G, G).

Although the foregoing embodiments have been described in some detail for purposes of clarity of understanding, the invention is not limited to the details provided. There are many alternative ways of implementing the invention. The disclosed embodiments are illustrative and not restrictive.

What is claimed is:
1. A nanopore based sequencing chip, comprising:
   an array of cells, wherein a cell comprises a nanopore sensor;
   a circuitry configured to:
      make a plurality of measurements of an electrical characteristic associated with the nanopore sensor;
      process the plurality of measurements of the electrical characteristic associated with the nanopore sensor; and
      perform data reduction to the plurality of measurements of the electrical characteristic associated with the nanopore sensor, comprising:
         determining that a first portion of the plurality of measurements of the electrical characteristic correspond to a single base call event at the nanopore sensor;
         determining a summary for the first portion of the plurality of measurements of the electrical characteristic, wherein determining the summary comprises: representing the first portion of the plurality of measurements of the electrical characteristic such that consecutive measurements of the electrical characteristic that are mapped to a threshold level are represented by a single magnitude value and either (i) a time duration or (ii) a count of the consecutive measurements of the electrical characteristic; and
         exporting the summary for the first portion of the plurality of measurements of the electrical characteristic.
2. A nanopore based sequencing chip, comprising:
   an array of cells, wherein a cell comprises a nanopore sensor;
   a circuitry configured to:
      make a plurality of measurements of an electrical characteristic associated with the nanopore sensor;
      process the plurality of measurements of the electrical characteristic associated with the nanopore sensor; and
      perform data reduction to the plurality of measurements of the electrical characteristic associated with the nanopore sensor, comprising:
         determining that a first portion of the plurality of measurements of the electrical characteristic correspond to a single base call event at the nanopore sensor;
         determining a summary for the first portion of the plurality of measurements of the electrical characteristic, wherein determining the summary comprises: determining that a second portion of the plurality of measurements of the electrical characteristic preceding the first portion of the plurality of measurements of the electrical characteristic correspond to an open channel state event at the nanopore sensor, and wherein determining that the second portion of the plurality of measurements of the electrical characteristic correspond to an open channel state event at the nanopore sensor is based at least in part on the second portion of the plurality of measurements of the electrical characteristic having a magnitude above a threshold level; and
         exporting the summary for the first portion of the plurality of measurements of the electrical characteristic.
3. The nanopore based sequencing chip of claim 1, wherein determining the summary comprises:
   representing the first portion of the plurality of measurements of the electrical characteristic with a magnitude parameter and a time parameter, wherein the time parameter corresponds to a duration of the first portion of the plurality of measurements of the electrical characteristic.
4. The nanopore based sequencing chip of claim 1, wherein determining the summary comprises:

representing the first portion of the plurality of measurements of the electrical characteristic such that consecutive measurements of the electrical characteristic that are mapped to a threshold level are represented by a single magnitude value and a count of the consecutive measurements of the electrical characteristic.

5. The nanopore based sequencing chip of claim 1, wherein determining the summary comprises:
representing the first portion of the plurality of measurements of the electrical characteristic such that consecutive measurements of the electrical characteristic that are mapped to a threshold level are represented by a single magnitude value and a time duration of the consecutive measurements of the electrical characteristic.

6. The nanopore based sequencing chip of claim 1, wherein determining the summary comprises:
extracting from the first portion of the plurality of measurements of the electrical characteristic information that enables the detection of a base call event.

7. The nanopore based sequencing chip of claim 1, wherein determining the summary comprises:
performing base calling on the first portion of the plurality of measurements of the electrical characteristic.

8. The nanopore based sequencing chip of claim 1, wherein the electrical characteristic comprises one of the following: a current, a voltage, a resistance, and a capacitance associated with the nanopore sensor or portions of the nanopore sensor.

9. A nanopore based sequencing chip, comprising:
an array of cells, wherein a cell comprises a nanopore sensor;
a circuitry configured to:
make a plurality of measurements of an electrical characteristic associated with the nanopore sensor;
process the plurality of measurements of the electrical characteristic associated with the nanopore sensor, wherein processing the plurality of measurements of the electrical characteristic associated with the nanopore sensor comprises: offsetting drift of magnitudes of the electrical characteristic over time such that distinct magnitude levels can be used as signature levels for identifying different base call events at the nanopore sensor; and
perform data reduction to the plurality of measurements of the electrical characteristic associated with the nanopore sensor, comprising:
determining that a first portion of the plurality of measurements of the electrical characteristic correspond to a single base call event at the nanopore sensor;
determining a summary for the first portion of the plurality of measurements of the electrical characteristic; and
exporting the summary for the first portion of the plurality of measurements of the electrical characteristic.

* * * * *